United States Patent [19]

Konishi et al.

[11] 4,310,420
[45] Jan. 12, 1982

[54] MOBILE PHASE SUPPLYING METHOD IN THE LIQUID CHROMATOGRAPHY AND APPARATUS THEREFOR

[75] Inventors: Hideki Konishi, Tokyo; Michiaki Sugawara, Hachioji; Muneo Saito, Tama, all of Japan

[73] Assignee: Japan Spectroscopic Co., Ltd., Tokyo, Japan

[21] Appl. No.: 127,994

[22] Filed: Mar. 4, 1980

[30] Foreign Application Priority Data

Mar. 14, 1979 [JP] Japan ................................. 54/29728

[51] Int. Cl.³ .............................................. B01D 15/08
[52] U.S. Cl. .................................... 210/659; 210/745; 210/101; 210/138; 210/198.2
[58] Field of Search ...................... 210/659, 198.2, 101, 210/138, 745

[56] References Cited

U.S. PATENT DOCUMENTS 3,862,038  1/1975  Takeuchi ........................... 210/198.2
4,032,445  6/1977  Munk .................................. 210/198.2
4,128,476  12/1978 Rock .................................. 210/198.2

OTHER PUBLICATIONS

Introduction to Modern Liquid Chromatography by Snyder et al. John Wiley and Sons, New York, pp. 101, 106, and 111–113, 1974.

*Primary Examiner*—John Adee
*Attorney, Agent, or Firm*—Browdy and Neimark

[57] ABSTRACT

A mobile phase supplying method in a liquid chromatography which is characterized in a disposition of a second plunger pump unit, in addition to the conventional way of employing one plunger pump unit (a first pump). The second plunger pump unit is disposed in series with the first plunger pump unit, being connected to the suction side of the first pump with the discharge side of the second pump, in order to synchronously supply the same amount of mobile phase discharged from the first pump to the suction side thereof by the second pump for the purpose of preventing the suction side of the first pump from being exposed to an occurrence of negative pressure. The apparatus for realizing the method is provided, in its double-pumped structure, with a connecting rod having on either end thereof a first and second plungers, between both pump units, which are synchronously and coaxially driven by a common driving system.

8 Claims, 4 Drawing Figures

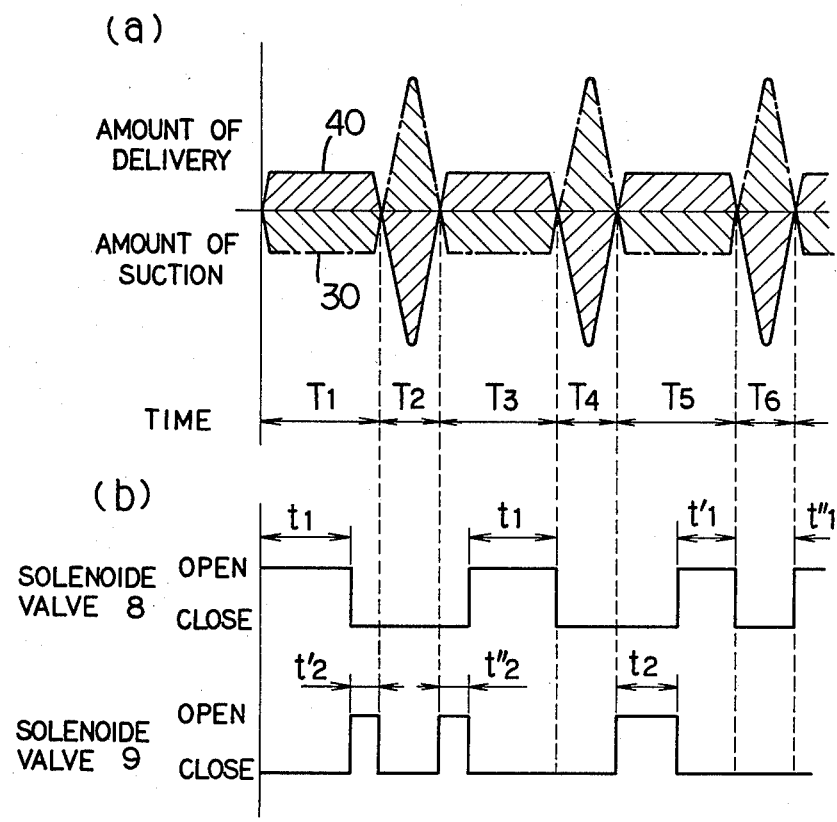

MOBILE PHASE SUPPLYING METHOD IN THE LIQUID CHROMATOGRAPHY AND APPARATUS THEREFOR

FIELD OF THE INVENTION

This invention relates to a mobile phase supplying method in the liquid chromatography and an apparatus therefor, and more particularly to the provision of a method and an apparatus therefor wherein a liquid chromatography apparatus, i.e., a liquid chromatograph, employing a single reciprocating type plunger pump is improved with respect to eliminating problems which may take place on the suction side of the plunger pump and are inherent to that pump, so that the mobile phase may be effectively supplied or delivered to the separation means such as a column.

BACKGROUND OF THE INVENTION

In recent years the liquid chromatography has been attracting attention of the people in the fields of chemistry, biology, medical science, etc., as one of the effective analyzing means.

The chromatography is aimed to, while delivering or supplying on one hand a solvent as mobile phase from a certain reservoir, by means of a supplying means such as a pump, to a separation means of the liquid chromatograph, for example a column, introduce on the other hand a sample, an object to be analyzed, into the separation means in order to develop and separate the sample with the aid of the mobile phase solvent for detecting the ingredients in the separated sample. In the liquid chromatography of this type, two or more different solvents have recently been utilized as the mobile phase, instead of the traditional method of employing one solvent, for the purpose of effectively eluting the aimed material from the separation means such as a column. Particularly the so-called gradient elution method capable of supplying the mixed solvents, while varying timewise the mixing ratio thereof in the course of supplying, to the separation means is given attention. A high performance liquid chromatography (HPLC), wherein the mobile phase solvent is rapidly supplied to the separation means under a high pressure of more than 50 Kg/cm$^2$ and sometimes exceeding 100 Kg/cm$^2$, is also developed for meeting the need or demand from some special uses requiring to effectively and speedily separate even a small amount of sample.

A liquid chromatograph for carrying out liquid chromatography of this kind is required as the apparatus therefor to have (1) ability to gradient elution capable of varying the mixing ratio of the solvents as a function of time accurately and freely, (2) constancy of the flow rate of the mobile phase solvent and delivery (transportation) thereof without pulsation to the separation means, and (3) capability of resisting high pressure, etc.

Various types of liquid chromatographs have been proposed for satisfying the above-mentioned conditions, in particular mobile phase supplying means of various kinds. Among them a liquid chromatograph employing a reciprocation type plunger pump for delivering or supplying the mobile phase is worthy of attention as a prior art in respect of its economical property.

Nevertheless it is far away from being ideal, still containing inherent problems to be solved. For supplying the mobile phase under low pulsation with a single plunger pump, a method of regulating the discharge amount constant, by controlling the speed of the plunger reciprocation, by means of shortening the time duration of suction on one hand and elongating the discharge time duration on the other hand, is generally adopted. This rapid suction of the mobile phase places the mobile phase on the suction side under pressure reduction, with a result of facilitating or accelerating the gas desolved in the mobile phase solvent to evaporate for forming bubbles, that is known as cavitation. It consequently degrades the accuracy (constancy) of the flow rate of the mobile phase solvent. It is required particularly in the gradient elution to operate the valves for sucking the individual solvents constituting mobile phase from the respective reservoir in such a short time, for example 0.1–0.2 second, wherein the plunger pump carries out the sucking of the solvent. Considering the response time required of the valves such as 10–20 msec., the operational error may be noticeably large, making the mixing of the mobile phase solvent (mixed solvent) at an accurate ratio difficult. Some attempts for solving the problem are seen, for example U.S. Pat. No. 3,985,021 and others, wherein electronic computer controlling, electric controlling system, etc. are adopted. In those propositions, controlling systems are mostly very complicated, leading the manufacturing cost very high as a whole. Otherwise each solvent reservoir must be equipped with an individual pump, which means plural pumps are required after all, resulting in high manufacturing cost and in difficulty of getting exact regulation of accurate mixing ratio of the plural solvents.

SUMMARY OF THE INVENTION

The present invention was made from such a background. The primary object of the invention is therefore to provide a novel method of mobile phase supplying in the liquid chromatography and an apparatus therefor, wherein problems which take place on the suction side of a reciprocation type plunger pump employed therein and inherent to the pump are entirely solved as well as eliminated.

The essential features of the invention reside in providing a first reciprocation type plunger pump for delivering a mobile phase of at least one solvent to the separation means in the liquid chromatograph, and a second reciprocation type plunger pump on the suction side of the first plunger pump for forming a series of the two pumps operating synchronously such that the second plunger pump supplies the same amount of the mobile phase as the discharge amount of the first plunger pump to that first plunger pump. By means of disposing those two plunger pumps in series, the sudden occurrence of negative pressure on the suction side of the first plunger pump can be perfectly eliminated, even when the first plunger pump executes a rapid sucking and a slow discharge, because the sudden sucking of the mobile phase by the first plunger pump is compensated synchronously by the second plunger pump. The formation of bubbles, a conventional problem, can be effectively prevented by this design. Even in the gradient elution, the suction time duration in the second plunger pump can be regulated suitably and preferably such that the suction time duration is longer than the discharge time duration, just in reverse to the regulation in the first plunger pump, for allowing the accurate regulation of the sucking amount ratio (mixing ratio) of the solvents from each reservoir within such suction time duration.

Such a mobile phase delivering or supplying can be realized by employing an apparatus of undermentioned structure comprising: (a) a first plunger pump unit, the discharge side thereof being connected to a piping which leads the mobile phase consisting of at least one solvent to separation means; (b) a second plunger pump unit, having the same capacity of suction and discharge as the first plunger pump unit, the suction side thereof being connected to a main suction pipe which flows the mobile phase formed by at least one solvent introduced from a reservoir and the discharge side thereof being connected to the suction side of the first plunger pump unit; (c) an axially slidable connecting rod situated between both plunger pump units, each plunger of the both plunger pump units being coaxially attached to the respective end of the connecting rod; and (d) a driving system for integrally reciprocating both plungers on either end of the connecting rod such that the first plunger pump unit and the second plunger pump unit are caused to carry out opposite operations to each other of sucking and discharging.

As described earlier, this invention has a great industrial meaning in enabling the mixing operation of two or more solvents, which constitute the mobile phase, to be accurate and easy, and consequently realizing the production cost reduction merit quite noticeably of the mobile phase supplying device of a liquid chromatograph. Those merits or advantages are brought about by employing an apparatus, a liquid chromatograph utilizing a reciprocation type plunger pump, which is further provided with another reciprocation type plunger pump connected in series with the former pump, so that the both pumps may effectively deliver or supply the mobile phase to the separation means without being bothered by the appearance of troublesome bubbles of gases on the suction side of the pump which delivers or supplies the mobile phase to the separation means.

BRIEF DESCRIPTION OF THE DRAWINGS

FIG. 4(a) is a graph showing the discharge amount and the suction amount of the two pumps in the embodiment; and FIG. 4(b) is an explanatory view for showing an example of opening and closing of solenoid valves in the embodiment.

DETAILED DESCRIPTION OF THE PREFERRED EMBODIMENTS

With reference to the appended drawings preferred embodiments will be described in detail hereunder.

Figure 1:
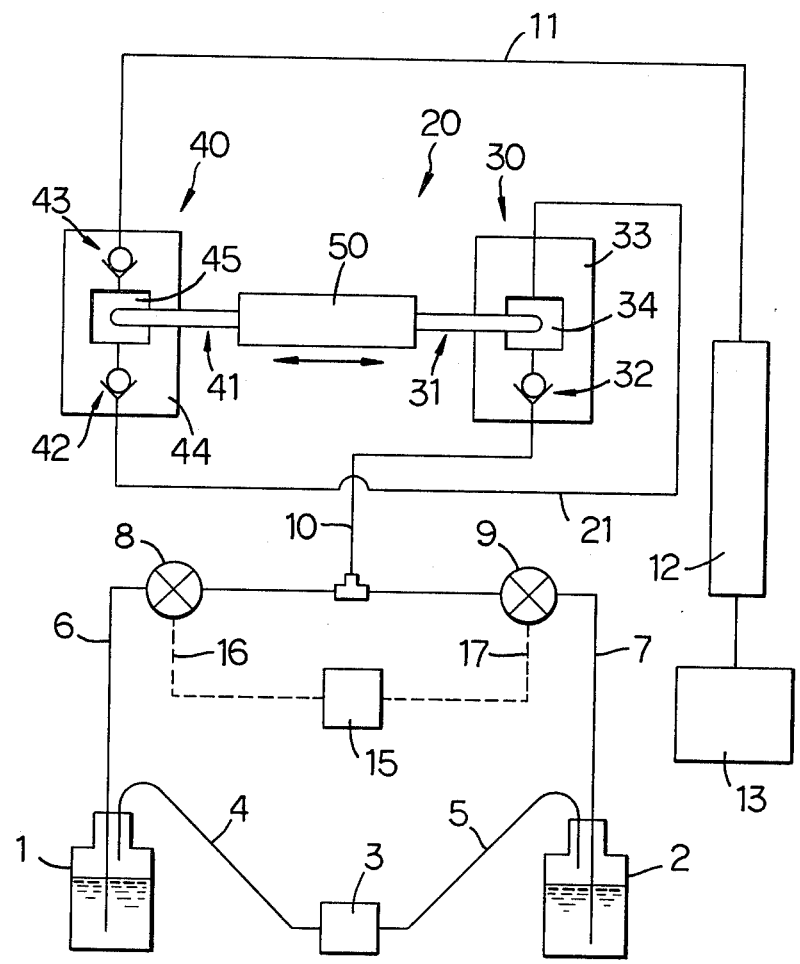
FIG. 1 is a block diagram schematically showing an embodiment of a liquid chromatograph provided with a mobile phase supplying device of this invention.

FIG. 1 is a schematical general view of an embodiment of a liquid chromatograph integrating a mobile phase supplying device or apparatus in accordance with this invention, wherein 1 and 2 are respectively a reservoir for a solvent different from each other. The reservoirs 1 and 2 may be either open or closed, but they may also be preferably sealed, as shown in FIG. 1, under a slight air pressure, for example 1.1–1.3 Kg/cm$^2$·abs or so, being communicated through a piping 4, 5 with a pressure accumulating chamber 3 in order to keep the constant pressure. However, the reservoirs 1 and 2 may be placed at a higher place, with an elevated potential energy instead of the pre-pressure system (3, 4, and 5), so that the solvents may be advantageously sucked by the action of the gravity alone. A pair of branch pipings 6, 7, starting from each reservoir 1, 2 are combined into, through each of a pair of solenoid valves 8, 9, a main suction pipe 10. Both valves 8, 9 are connected, through electric wiring 16, 17, to a programmer 15. Therefore, assume $t_1$ is a time duration wherein the solenoid valve 8 is open and the solenoid valve 9 is closed, and $t_2$ is a time duration in a reversed state, then the time ratio $t_1/t_2$ indicates the mixing ratio of the two solvents, so long as the sucking speed is constant. Each solvent sucked through such valves 8, 9 at a predetermined ratio is introduced, through the main suction pipe 10, to a pumping system 20. A predetermined mobile phase is formed by mixing the two solvents at a predetermined ratio in the main suction pipe 10. Here a case wherein two kinds of solvents are supplied is illustrated, but the kinds of the solvents may be increased to three or more. The number of reservoirs, branch pipings, solenoid valves, etc., have to be increased in response to the number of the solvents. The solenoid valve is not limited to be disposed on each branch piping 6, 7 as in this embodiment, it may be, for example, a cross valve which is capable of switching many kinds of solvents, being situated on a confluent point or junction of a plurality of branch pipings.

The pumping system 20 is integrally composed of a low pressure pump 30 (a pump unit of reciprocation plunger type) as a low pressure mobile phase supplying means, a high pressure pump 40 (a pump unit of reciprocation plunger type) as a high pressure mobile phase supplying means, a connecting rod 50 having on either end thereof a plunger 31, 41 attached thereto, and a later described but not shown driving means or system for reciprocating the connecting rod 50 in the axial direction thereof (marked with an arrow). The suction side of the low pressure pump 30 is connected to the main suction pipe 10. The discharge side of the low pressure pump 30 and the suction side of the high pressure pump 40 are connected to each other by a connecting pipe 21. So the mobile phase introduced into the low pressure pump 30 from the main suction pipe 10 through a check valve 32 is supplied, due to synchronized discharging action of the plunger 31 and sucking action of the plunger 41, toward the high pressure pump 40 through the connecting pipe 21 for being delivered into the high pressure pump 40 through another check valve 42. The discharge side of the high pressure pump 40 is connected to a mobile phase supplying pipe 11. So the mobile phase delivered into the high pressure pump 40 is, owing to the discharging action of the plunger 41, discharged into the mobile phase supplying pipe 11 through a third check valve 43, and transported in turn to a column 12, i.e., separation means of a liquid chromatograph. A sample is injected and separated by such a mobile phase, for being detected of its ingredients by means of a suitable well-known detecting means 13.

Figure 2:
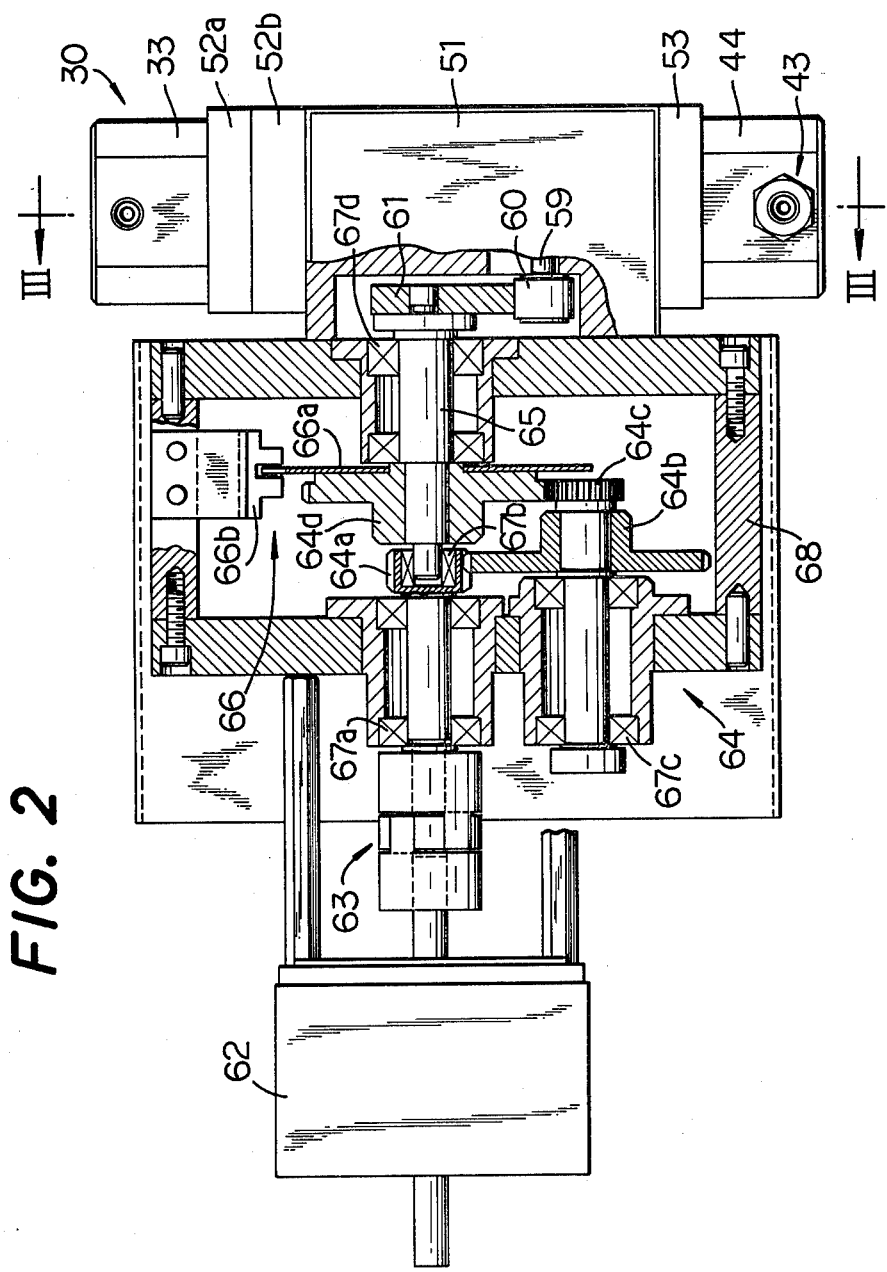
FIG. 2 is a detailed plan view, partly being broken away, of a pumping system in FIG. 1.
Figure 3:
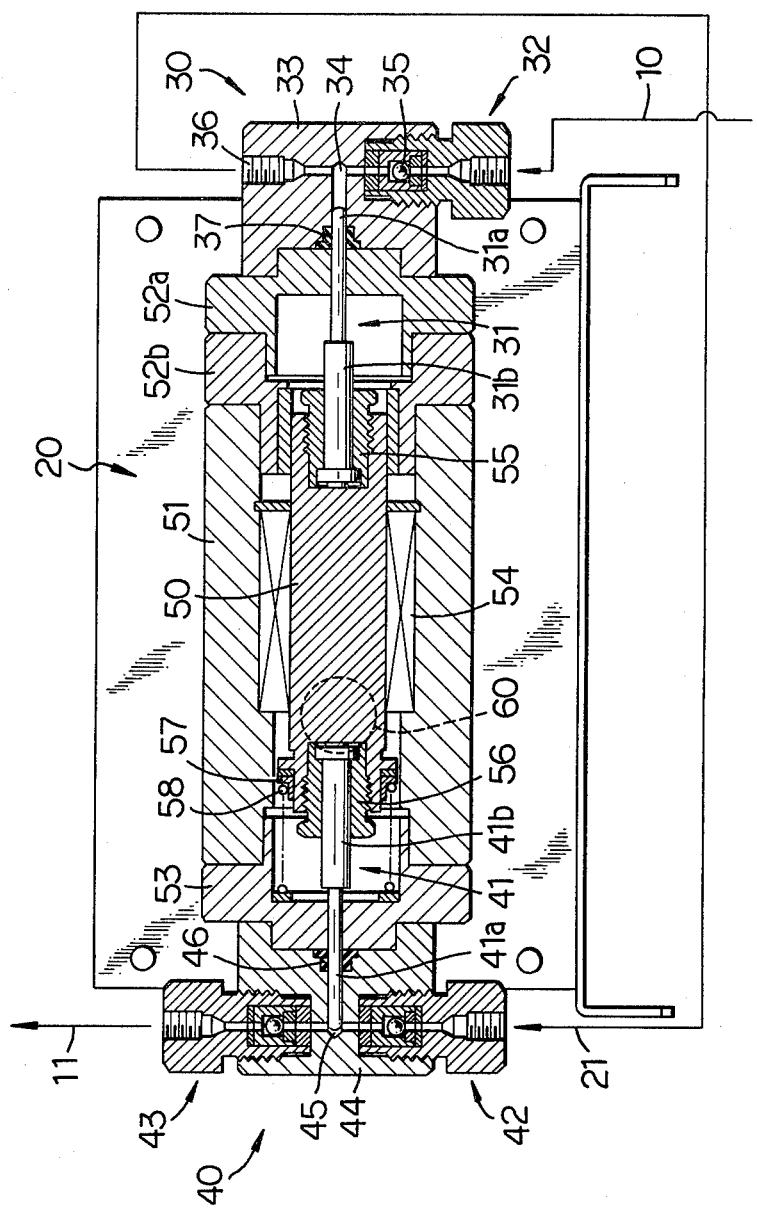
FIG. 3 is a sectional view of FIG. 2 taken along the line III—III.

The pumping system 20 in this embodiment will be described further in detail with reference to FIGS. 2 and 3. FIG. 2, shows a plan view partly broken away of the pumping system 20. FIG. 3 shows a cross-sectional view of the pump portion. The low pressure pump 30 has a pump head 33 in which a pumping chamber 34 is formed. A rod portion 31a on the end of the plunger 31 executes pumping action in this pumping chamber 34 by the reciprocal movement thereof. The pumping chamber 34 is communicated with the main suction pipe 10 through the check valve 32, which is of conventional type in this sort of pump, for allowing only the flow-in of the mobile phase from the main suction pipe 10 to the pumping chamber 34 by the moving action of a ball 35. The mobile phase discharged from the pumping chamber 34, unlike in case of the suction side, is delivered, through a discharge outlet 36 connected to the chamber 34, to the connecting pipe 21 which is extended from the outlet 36 for being introduced to the high pressure pump 40. Numeral 37 designates a seal.

The high pressure pump 40 is, just like the low pressure pump 30, provided with a pump head 44 and a pumping chamber 45 formed therein. A rod portion 41a on the end of the plunger 41 executes the pumping action through the reciprocal movement thereof in the pumping chamber 45. The rod portion 41a of the plunger 41 is similarly made with the rod portion 31a of the plunger 31 in the low pressure pump 30, with the object that the high pressure pump 40 has through its design the same capacity of suction and discharge as the low pressure pump 30. The pumping chamber 45 is, through those valves 42, 43, connected to the connecting pipe 21 and the mobile phase supplying pipe 11, so that the mobile phase may be flowed one way from the connecting pipe 21 through the pumping chamber 45 into the mobile phase supplying pipe 11. Numeral 46 designates likewise a seal.

Both pumps 30, 40 are respectively secured, via flanges 52a and 52b as to the former and a flange 53 as to the latter, to either end portion of a cylindrical body 51 accommodating the connecting rod 50. The connecting rod 50 is axially slidably carried in the inner hollow portion of the cylindrical body 51 via a slidable bearing 54 (linear motion bearing). On one end of the body 51 a rod-like base portion 31b of the plunger 31 in the low pressure pump 30 is coaxially disposed with a nut 55. On the other end of the body 51 a rod-like base portion 41b of the plunger 41 in the high pressure pump 40 is coaxially disposed with a nut 56. On the end portion of the connecting rod 50, where the plunger 41 of the high pressure pump 40 is attached, a spring seat 57 is disposed around the outer periphery of the end portion. Between the spring seat 58 and the bottom of a recess portion formed on the inner side of the flange 53 a compression spring 58 is disposed for constantly biasing the connecting rod 50 rightwardly in FIG. 3. The spring 58 is illustrated in its compressed state in FIG. 3.

As can be clearly seen in FIG. 3, on either end of the connecting rod 50 the plunger 31, 41 of the respective pump 30, 40 is coaxially attached, and the rod portion 31a, 41a of each plunger 31, 41 is respectively pierced through the flanges 52a and 53 as far as the inside of the pumping chamber 34, 45. An integral reciprocal movement in the axial direction of those three members of connecting rod 50 and the plungers 31, 41 causes, in each pump 30, 40, exactly reversed actions of suction and discharge. In order to actuate this axial reciprocative movement, a driving system for shifting the connecting rod 50 leftwardly is disposed. In other words, the leftwardly directed shifting of the connecting rod 50 and the rightwardly biased spring force on the same give rise to the reciprocal movement of the connecting rod 50.

In this driving system, a shaft 59 secured to the connecting rod 50, at the rear side of the drawing paper in FIG. 3 and on the left side of the connecting rod 50 in FIG. 2, is provided on the outer end thereof a cam follower (bearing) 60; and the cam follower 60 is, owing to the rotation of a suitably shaped cam 61 which is actuated by a stepping motor 62 through a reduction gear train 64 consisting of gears 64a–64d, pushed or shifted downwards in FIG. 2 (leftwards in FIG. 3) at a predetermined speed. The suitably shaped cam 61 which abuts the cam follower 60 is easily designed and machined by modern computer machining technology. The rotation of the stepping motor 62 is transferred, while being reduced by the reduction gear train 64 which is connected with the motor 62 through a coupling 63, to a cam shaft 65. The shifting speed of the connecting rod 50 in the leftward direction in FIG. 3 is determined by the shape and the rotational speed of the cam 61 attached to the cam shaft 65, which is regulated at a desirable speed by the stepping motor 62 and the gear train 64.

Furthermore an encoder consisting of a chopper 66a secured to the gear 64d, on which the cam shaft 65 is fixed, and a photo-coupler 66b functions to detect the state of driving the pumps 30, 40 by the cam 61. The result of the detecting is input as a signal to the programmer 15 in FIG. 1 for being utilized to regulate the solenoid valves 8, 9. And the signal from the encoder 66 is also utilized for regulating the driving of the stepping motor 62 (regulation of the rotational speed). Numeral signs 67a–67b designate respectively a bearing, and numeral 68 designates a supporting member. In place of the stepping motor 62, any other driving sources such as a servomotor which is capable of freely varying the rotational speed is permissible.

In this pumping system 20, each plunger 31, 41 of the low and high pressure pumps 30, 40 executes (carries out) respectively an entirely reversed pumping action in response to the reciprocative movement of the connecting rod 50. When the connecting rod 50 is, owing to the urging by the cam 61 and the cam follower 60, leftwardly shifted in FIG. 3 at a predetermined speed, discharge of the mobile phase occurs in the high pressure pump 40 while suction of the mobile phase occurs in the low pressure pump 30. When the connecting rod 50 reaches the extreme left, it begins to rightwardly move by the action of the compression spring 58, causing contrarily the low pressure pump 30 to discharge and the high pressure pump 40 to suck. The high pressure pump 40 which supplies the mobile phase to the column 12 is furnished at each sucking operation thereof with the same amount of mobile phase by the low pressure pump 30, so a noticeable occurrence of negative pressure can be prevented, thereby cavitation would not take place, even when a sudden sucking action occurs on the suction side of the high pressure pump 40. It effectively prevents the appearance of bubbles of gases there.

In this embodiment the amount of the mobile phase discharge in the low pressure pump 30 per each reciprocation of the plunger 31 is made equal to the amount of the mobile phase suction in the high pressure pump 40 per each reciprocation of the plunger 41; and the time duration of the mobile phase discharging action in the low pressure pump 30 in response to the reciprocative movement of the connecting rod 50 is made naturally equal to the time duration of the mobile phase sucking action in the high pressure pump 40 and vice versa, i.e., the time duration of sucking in the low pressure pump 30 and that of discharging in the high pressure pump 40 are equalized. By this design the object of this invention can be effectively achieved, however, this invention is by no means limited to this design or structure only. For example, the low pressure pump 30 and the high pressure pump 40 may be separately disposed such that the low pressure pump 30 can reciprocate several times while the high pressure pump 40 does a single reciprocation movement for supplying the predetermined amount of the mobile phase to the latter in the meantime.

For the purpose of achieving the low pulsative delivery of the mobile phase, which is highly desirable in liquid chromatography, the time duration $T_{s1}$ required in the sucking action of the mobile phase in the high pressure pump 40 (first pump) which should deliver the mobile phase to the column 12 is preferably made not longer than the time duration $T_{d1}$ required in the discharging action, i.e., $T_{s1} \leq T_{d1}$, so that the conventional rapid suction and the slow discharge may be fulfilled by controlling the discharge amount of the mobile phase throughout the slow discharging constant as usual. Driving of the high pressure pump 40 in such a manner can be easily realized by various well-known methods.

In the low pressure pump 30, just like in the high pressure pump 40, it is also desirable that the time duration $T_{s2}$ required in the suction is made equal or longer than the time duration $T_{d2}$ required in the discharge so that the slow sucking and the rapid discharge may be secured. The above-mentioned way of driving of the pumps 30, 40 is greatly meritorious. That is to say, the elongation of the suction time duration in the low pressure pump 30 enables the solenoid valves 8, 9 disposed on the way of the pipes 6 and 7 to advantageously open and close within the elongated time duration with little consideration on the possible errors depending on the length of the time duration of the valve response. It makes possible to suck from each reservoir 1, 2 a predetermined amount of the solvent, and in turn to flow the mixture of the mobile phase solvent which has been mixed at an accurate mixing ratio.

In the apparatus of this embodiment, the above-mentioned ideal way of driving of the pumps 30, 40 is effectively realized, because each plunger 31, 41 driven by the connecting rod 50 can carry out the synchronous and just reversed operation, i.e., suction and discharge. FIG. 4(a) illustrates the flow profile of mobile phase delivery by the apparatus, in a graph showing the amount of suction and discharge by each pump 30, 40, wherein the apparatus of the embodiment is used in a preferable way of pump driving. In the figure the solid line shows the discharge/suction curve in the high pressure pump 40 and the one-dot chain line shows the discharge/suction curve in the low pressure pump 30. While the high pressure pump 40 executes a slow or long time duration discharge of constant amount, the low pressure pump 30 does a slow suction of constant amount in order to suck thereinto the mobile phase of the same amount as that discharged by the high pressure pump 40. When the high pressure pump 40 does a rapid suction, the same amount of the mobile phase sucked is supplied by the low pressure pump 30 at its rapid discharge.

In this embodiment which repeats the above-mentioned discharge/suction pattern of both pumps 30, 40, while the low pressure pump 30 carries out the discharging action ($T_2, T_4, \ldots$) each solvent in each reservoir 1, 2 is preferred to be prevented from flowing into the low pressure pump 30 by the solenoid valves 8, 9 maintained closed. For preparing a mixed solvent of a certain mixing ratio or a mixed solvent which timewise varies its mixing ratio for a gradient elution, an undermentioned method is preferably adopted, that is, the solenoid valves 8, 9 are opened-and closed during the time duration ($T_1, T_3, T_5, \ldots$) of the sucking action by the low pressure pump 30 and consequently the kind of solvent sucked from each reservoir 1, 2 is switched or converted alternately according to the predetermined time ratio (when the sucking rate is constant) or the predetermined flow amount ratio, so that the low pressure pump 30 may in order suck the predetermined amount of the predetermined solvent.

An example of such a pattern of alternately switching solenoid valves is illustrated in FIG. 4(b). In this example the sum of the opened time duration ($t_1 = t_2$) of each solenoid valve 8, 9 is longer than the time duration ($T_1, T_3, \ldots$) of sucking of the low pressure pump 30, and the valve 8 is operated in opened state for the predetermined time duration $t_1$ while the valve 9 is operated in opened-state for the time duration of $t_2$ which is the sum of the remaining suction time duration ($T_1 - t_1 = t'_2$) and the predetermined time duration $t''_2$ out of the next cycle of the sucking time duration $T_3$. In such a manner a mixed solvent (mobile phase) of the predetermined mixing ratio is prepared. It can be formulated as $t_2 = t'_2 + t''_2$. On the other hand, the valve 8 is also operated, just like the valve 9, ranging over the time duration of the suction of the low pressure pump 30. Then that operation of the valve 8 should be regulated as to satisfy the formula $t_1 = t'_1 + t''_1$. Furthermore, in case the valves 8 and 9 are operated ranging over the time duration of the suction ($T_1, T_3, T_5, \ldots$), the sum of the valve-operated time durations ($t_1 + t_2$) may sometimes be shorter than the time duration of the suction. In such a case each valve 8, 9 is similarly operated as described earlier.

As a concrete method of regulating the mixing ratio of two or more kinds of solvents according to a certain flow ratio, a method wherein predetermined amount of each solvent is in order supplied according to a certain ratio between the numbers of pulses driving the stepping motor 62 (suction amount per one pulse is determined to be constant) is proposed. In this case the valves 8 and 9 are also regulated, in respect of their opening and closing, by the signals from the controlling system for the stepping motor 62.

Although one embodiment of this invention, with references to some modified examples, was described, many other variations, improvements, etc., are of course possible to be made by those skilled in the art without departing from the spirit and scope of this invention. For example, this invention is applicable to a case wherein only one solvent is supplied as a mobile phase to the separation means such as a column 12, irrespective of this invention being preferably designed to be utilized in preparing a mixed solvent, as a mobile phase, which has been mixed of solvents more than one kind at a certain fixed ratio or a timewise variable mixture of solvents used in the gradient elution. As another example, various well-known driving systems are practicable in the reciprocative movement of the connecting rod 50, in place of the above described driving system including the cam 61 and the cam follower 60, that is, any driving source is allowable to directly, or indirectly via a transmitting means such as a gear(s), drive the connecting rod 60 so as to reciprocate the same. As a third example, a suitable solvent mixing means may be disposed at the junction of the branch pipes 6 and 7 or downstream of the same on the way of the main suction pipe 10 for obtaining a better mixing of the solvents from the reservoirs 1 and 2.

What is claimed is:

1. A method of supplying the mobile phase to a liquid chromatograph wherein said mobile phase consists of a predetermined mixture of a plurality of solvents each contained in separate reservoir means; providing valve means and controlling the flow of each solvent out of its reservoir means using said value means;

providing a first reciprocation type plunger pump to supply said mobile phase and a sample therein to a liquid chromatograph;

providing a second reciprocation type plunger pump to supply said mobile phase to the suction side of said first pump;

synchronously driving both said pumps to secure a supply of said mobile phase to the first pump by supplying the same amount thereof discharged by said second pump;

controlling said valve means such that all of said solvents are prevented from flowing into said second pump while said second pump is carrying out its discharging operation; and controlling the second pump when it is carrying out its sucking operations of the solvents from each reservoir via said valve means according to a predetermined time ratio or according to a predetermined flow amounts ratio, whereby said predetermined mixture of said plurality of solvents in said mobile phase comprises predetermined amounts of and predetermined kinds of said solvents to be sucked into said second pump.

2. The method in accordance with claim 1, wherein the discharge amount of said mobile phase in one reciprocation of said second pump is equal to the suction amount of said mobile phase in one reciprocation of said first pump.

3. The method in accordance with claim 2, wherein both pumps are driven such that the time duration of the discharging operation by said second pump is equal to the time duration of the sucking operation by said first pump.

4. The method in accordance with claim 2, wherein the ratio; $T_{s1}/T_{d1}$ between the time duration; $T_{s1}$ required for the sucking operation and the time duration; $T_{d1}$ required for the discharging operation of said first pump is one or less.

5. The method in accordance with claim 1, 2, 3 or 4, wherein the ratio; $T_{s2}/T_{d2}$ between the time duration; $T_{s2}$ required for the sucking operation and the time duration; $T_{d2}$ required for the discharging operation of said second pump is one or more.

6. In a liquid chromatograph of the type wherein a mobile phase which consists of a predetermined mixture of a plurality of solvents is supplied to liquid chromatographic separation means for separating a sample introduced into the mobile phase, a mobile phase supplying apparatus comprising:

a first plunger pump unit and means to connect the discharge side thereof to said separation means;

a second plunger pump unit of substantially the same capacity of discharge and suction as that of said first plunger pump unit, a plurality of reservoirs, one for each of said plurality of solvents;

valve means to control the flow of solvents out of said reservoirs;

means to control said valve means such that all of said solvents are prevented from flowing into said second pump while said second pump is carrying out its discharging operation;

the discharge side of said second pump unit being connected to the suction side of said first pump unit;

an axially slidable connecting rod between both of said plunger pump units, means to axially attach the ends of said rod to the plunger of each of said pump units, respectively;

a driving system for synchronously and reciprocally driving both plungers via said connecting rod to cause said first pump unit and said second pump unit to carry out reversed actions, sucking and discharging, respectively; and control means for said valve means to cause the time duration of the second pump carrying out its sucking operations of the solvents from each reservoir to be according to a predetermined time ratio or according to a predetermined flow amount ratio, whereby said predetermined mixture in said mobile phase comprises predetermined amounts of and predetermined kinds of said solvents to be sucked into said second pump.

7. The apparatus in accordance with claim 6, wherein said driving system is composed of a cam follower mounted on said connecting rod, a cam abutted on said cam follower for urging said connecting rod axial by, and means for rotating said cam at a predetermined speed.

8. The combination of claim 6, wherein said control means comprises an optical encoder associated with the driving system for said connecting rod.

* * * * *